United States Patent
Martínez Palou et al.

(10) Patent No.: US 10,384,247 B2
(45) Date of Patent: Aug. 20, 2019

(54) PROCESS FOR OBTAINING IONIC AMINO ACID ESTERS

(71) Applicant: INSTITUTO MEXICANO DEL PETRÓLEO, Mexico City (MX)

(72) Inventors: Rafael Martínez Palou, Mexico City (MX); Ricardo Cerón Camacho, Mexico City (MX); Alba Adriana Vallejo Cardona, Mexico City (MX); Romeo Jesús Reyes Ávila, Mexico City (MX); Juan de la Cruz Clavel Lopez, Mexico City (MX); César Bernal Huicochea, Mexico City (MX); Mario Ramiréz De Santiago, Mexico City (MX); Jorge Arturo Aburto Anell, Mexico City (MX)

(73) Assignee: Instituto Mexicano Del Petroleo, Mexico City (MX)

( * ) Notice: Subject to any disclaimer, the term of this patent is extended or adjusted under 35 U.S.C. 154(b) by 402 days.

(21) Appl. No.: 14/847,727

(22) Filed: Sep. 8, 2015

(65) Prior Publication Data
US 2016/0068471 A1   Mar. 10, 2016

(30) Foreign Application Priority Data
Sep. 8, 2014 (MX) .................... MX/a/2014/010730

(51) Int. Cl.
| | | |
|---|---|---|
| C07C 209/68 | (2006.01) | |
| B01D 17/04 | (2006.01) | |
| B09C 1/08 | (2006.01) | |
| C07D 209/20 | (2006.01) | |
| C07C 227/02 | (2006.01) | |

(52) U.S. Cl.
CPC .............. B09C 1/08 (2013.01); B01D 17/047 (2013.01); C07C 227/02 (2013.01); C07D 209/20 (2013.01)

(58) Field of Classification Search
None
See application file for complete search history.

(56) References Cited

U.S. PATENT DOCUMENTS

2004/0162434 A1* 8/2004 Hatakeda .............. C07C 227/08
548/339.1

OTHER PUBLICATIONS

Arai, Isamu et al., "A Simple and Convenient Method for Esterification of Trytophan and Other Amino Acids", J. Org. Chem., 1983, vol. 48, pp. 121-123.
Penney, Christopher L. et al., "A Simple Method for the Synthesis of Long-Chain Alkyl Esters of Amino Acids", J. Org. Chem., 1985, vol. 50, pp. 1457-1459.
Ceron-Camacho, Ricardo et al., "Efficient Microwave-Assisted Synthesis of Ionic Esterified Amino Acids", Molecules, 2011, vol. 16, pp. 8733-8744.
Martinez-Palou, Rafael et al., "Study of the formation and breaking of extra-heavy-crude-oil-in-water-emulsions—A proposed strategy for transporting extra heavy crude oils", Chemical Engineering and Processing: Process Intensification, 2015, vol. 98, pp. 112-122.
Kawase, Tokuzo et al., "A Novel Synthesis of N-Alkoxycarbonyl Amino Acids and Surfactant Properties of Their Sodium Salts", Journal of Oleo Scieve, 2010, vol. 59, No. 4, pp. 191-201.
Gibson, Sarah et al., "Concurrent esterification and N-acetylation of amino acids with orthoesters: A useful reaction with interesting mechanistic implications", Tetrahedron Lett., Dec. 22, 2010, vol. 51, No. 51, pp. 6737-6740.
Zhao, Hua et al., "Microwave-Assisted Esterification of N-Acetyl-L-Phenylalanine Using Modified Mukaiyama's Reagents: A New Approach Involving Ionic Liquids", International Journal of Molecular Sciences, 2008, vol. 9, pp. 33-44.
Sureshbabu, Vommina et al., "Microwave irradiation accelerated rapid, efficient and high yield esterification of Boc-amino acid to Merrifield resin mediated by KF", Indian Journal of Chemistry, Sep. 2007, vol. 46B, pp. 1466-1469.
Sathe, Manisha et al., "An efficient method for the esterification of amino acids using silica chloride", Catalysis communications, 2006, vol. 7, pp. 644-646.
Leyendecker et al., "Ligand Effects in Enantioface Differentiating 1,4 Addition to 1,3 Diphenyl-2 Propen-1 One", Tetrahedron Letters, 1983, vol. 24, No. 33, pp. 3513-3516.
Brook, Michael A. et al., "A Simple Procedure for the Esterification of Carboxylic Acids", Synthesis, Mar. 1983, pp. 201-203.
Paquet, A., "Preparation of some long-chain N-acyl derivatives of essential amino acids for nutritional studies", Canadian Journal of Biochemistry, vol. 58, No. 7, pp. 573-576.
Martinez-Palou, R. et al., . Desarrollo de un proceso integral para el transporte de crudos pesados. Estudio para a formación de emulsiones O/W mediante biotensoactivos. Rev. Ing. Petrol. 2014, 54(4), 233-247 (abstract only).
Rivera, J.C. Estudio del proceso de formación y ruptura de emulsiones mediante emulsiones inversas (O/W) para el transporte de crudos pesados. Thesis, Superior Technol. Inst. of Misantla, Feb. 2013 (abstract only).

* cited by examiner

*Primary Examiner* — Po-Chih Chen
(74) *Attorney, Agent, or Firm* — Jason P. Mueller; Adams and Reese LLP

(57) ABSTRACT

Embodiments of the present invention provide for efficient methods and processes for preparing ionic amino acid esters from a specific synthesis route. The disclosed embodiments consist of a single reaction step: reacting a natural or synthetic unprotected amino acid with an aliphatic, branched or aromatic fatty alcohol of even or odd number of carbon atoms from 6 to 20 with or without unsaturation(s), in stoichiometric amounts, in the presence of an organic acid (HX) like carboxylate, mesylate, tosylate or sulfonate, employed as catalyst and under conventional heating (CC) of 1 to 3 hours at a temperature in the range of approximately 60 to 150° C. and pressure the range of approximately 0 to approximately 250 psi; the product obtained is cooled and recrystallized from ethanol.

29 Claims, No Drawings

PROCESS FOR OBTAINING IONIC AMINO ACID ESTERS

CROSS-REFERENCE TO RELATED APPLICATIONS

This application is based on and claims the benefit of priority from Mexican Patent Application No. MX/a/2014/010730, entitled IMPROVED PROCESS FOR OBTAINING AMINO ACID ESTERS, which is hereby incorporated in its entirety by reference thereto.

FIELD OF THE INVENTION

The present invention relates to the synthesis of amphiphilic derivatives of amino compounds with surface properties.

BACKGROUND OF THE INVENTION

The amino acid esters are long chain compounds with nutritional (Paquet, A. *Can. J. Biochem.* 1980, 58, 573-576) and surfactant applications (Kawase, T.; Nishioka, Y.; Oida, T. *J. Oleo Sci.* 2010, 59, 191-201). The synthetic routes for such kind of compounds are pretty limited and required the use of short-chain, liquid alcohols as raw materials (Brook, M.; Chan, T H. *Synthesis* -Stuttgart 1983, 201-203); but fail to use solid alcohols as is the case of fatty alcohols required to obtain compounds of amphiphilic nature.

Conventional synthesis methods are very aggressive for the environment because they use very strong and corrosive acid catalysts (Yang, Q.; Wang, X.-J.; Li, Z Y; Sun, L.; You, Q D. *Synth Commun.* 2008 38, 4107-4115; Penney, C. L; Shah, P; Landi, S J. *Org Chem.* 1985, 50, 1457-1459), very toxic and dangerous reagents such as p-toluenesulfonyl chloride (Arai, I.; Muramatsu, I J. *Org Chem.* 1983, 48, 121-123), diazomethane (Leyendecker, F.; Jesser, F.; Laucher, D. *Tetrahedron Lett.* 1983, 24, 3513-3516) or ortho esters (Gibson, S.; Romero, D.; Jacobs, H K; Gopalan, A S. *Tetrahedron Lett.* 2010, 51, 6737-6740).

It is common that the synthesis reactions require multiple steps (protection, esterification and deprotection) obtaining products with low yield (Zhao H.; Song Z.; Cowins J V.; Olubajo, O. *Int. J. Mol. Sci.* 2008, 9, 33-44; Sureshbabu W.; Kantharaju; Krishna G C. *Int. J. Chem. B.* 2007, 46, 1466-1469) or by using an inert atmosphere (Sathe M.; Kaushik M P. *Catal. Commun.* 2006, 7, 644-646).

Recently, a strategy of synthesis in one step by microwave irradiation and where a yield of about 60-80% is obtained by using an excess of alcohol (Cerón-Camacho, R.; Aburto, J.; Montiel L. E.; Flores, E A.; Cuellar, F.; Martinez-Palou, R. *Molecules,* 2011, 16, 8733-8744).

Compared to such method, the present invention turns out to be attractive because the use of a microwave reactor is avoided, the reagents are used only in stoichiometric ratio and with a slight excess of acid functions both as catalyst and reactant. Therefore, the reaction is easily scalable and product performance is roughly comparable and even higher than 80% using both short as long chain alcohols.

SUMMARY OF THE INVENTION

Embodiments of the present invention relate to the field of organic chemistry and to a synthesis process of preparing ionic amino acid esters using a simple pressure reactor of glass or steel reactor with a vent attachment; which allows to carry out chemical reactions under autogenous pressure without hazardous giving high yields over conventional synthesis methods such as pressurized flasks, ultrasound and microwaves. These compounds are of great interest because of the wide variety of applications, particularly but not exclusively, to be used as biosurfactants for breaking oil-water emulsions, water in oil, mixed; or in washing the crude oil contained in contaminated soils.

In embodiments of the present invention, ionic amino acid esters may be obtained in a single reaction stage or "one pot" following the green chemistry statements by simultaneous esterification and protonation of the amino group to generate an ammonium cation group. Additionally, none or a minimum amount of waste is generated, since all reagents are part of the product, and its purification is easier or unnecessary since the atom economy is between 86-95% according to the principles of green chemistry.

DETAILED DESCRIPTION OF THE INVENTION

Embodiments of the present invention relate to the synthesis of amphiphilic derivatives of amino compounds with surface properties, which favors: 1) emulsification of oil in water phase, such as oil, reducing its viscosity and improving the transport properties; 2) emulsifying the oil phase in an aqueous phase which allows washing of contaminated soil and 3) increase the oil-water interfacial tension and allows the breakdown of oil in water emulsions or water in oil emulsions commonly encountered during production, transport and refining of oil. Also, the ionic amphiphilic derivatives of amino acids such as, but not limited to, glycine, alanine and tryptophan may favor breaking oil-water emulsions, water-oil and mixed.

In embodiments, these amphiphilic compounds may be synthesized by an esterification reaction in acid medium using conventional heating or efficiently using pressure reactors. This may be an affordable alternative to a microwave equipment; since a pressure reactor has a pressure release latch preventing accidental explosion due to overpressurization. They are easy to operate and offer reproducibility by facilitating scaling reactions, it is sustainable because it saves energy compared to other types of reactors and their maintenance is minimal, and is more economical. Therefore, the preparation of amino acid derivatives compounds of the present invention employing a pressure reactor vent with an attachment proves to be very attractive, since the product is obtained in a single step and purification is simple.

In addition, this type of amphiphilic compounds derived from amino acids have the attraction of being biodegradable, non-toxic and inexpensive, since its raw materials are found in biomass. So, they may also represent a technological and ecological alternative in various industries such as food, pharmaceutical, chemical, cosmetic and petroleum.

Embodiments of the present invention provide an efficient method for obtaining ionic esters of long chain amino acids from amino acids such as, although not exclusively limited to, glycine, alanine and tryptophan, because in principle it can be used any other natural or synthetic amino acid. In exemplary embodiments, the reaction may occur with long chain fatty alcohols of 6 to 20 carbon atoms, preferably 8 to 18 carbon atoms, where the alcohol may be linear, branched or aryl; or contain unsaturation(s). This procedure is general and may be employed using short chains (liquid or solid at room temperature alcohols) aliphatic alcohols and aryl alcohols may also be used such as ethanol or benzyl alcohol.

In embodiments of the present invention, the product may be obtained in a single stage reaction with the use of a pressure reactor with a vent attachment, without the use of solvents and using organic acid catalysts. This procedure may be performed using conventional heating; and the reaction conditions may be achieved using pressurized reactors as Q-tube, QuianCap, Parr reactors, Büchi, etc. Moreover, in exemplary embodiments, the components of the reactive part of the product; wherein the amino acid and alcohol are mixed in stoichiometric amounts with a slight excess of acid functions as a catalyst, are less than 2 mol equivalents and preferably from 1.1 to 1.6 mol. This reduces the formation of residues, which facilitates purification of said compounds and this makes the process easier to clean or purification unnecessary.

Also, certain amphiphilic compounds have the property of reducing the surface tension and to encourage integration of two immiscible liquids such as water and crude oil.

Embodiments of the present invention relate to the field of organic chemistry and to a process of synthesis of ionic amino esters using a simple pressure reactor composed by a glass or steel reactor with a vent attachment; which allows to develop chemical reactions under autogenous pressure without hazardous giving high yields over conventional synthesis methods such as pressurized flasks, ultrasound and microwaves. These compounds are of great interest since they have a wide variety of applications, particularly but not exclusively, to be used as biosurfactants for breaking oil-water emulsions, water in oil, or more complex emulsions; or in washing the crude oil contained in contaminated soils.

In embodiments of the present invention, ionic amino acid esters may be obtained in a single reaction stage or "one pot" by simultaneous esterification and protonation of the amino group to generate an ammonium cation group. Additionally, a minimum amount of waste may be generated, since all reagents are part of the product, and therefore purification is unnecessary or minimum. Therefore, they have a high value of atom economy, between 88-95%, according to the principles of green chemistry.

In exemplary embodiments, the amino acid esters may be obtained by reaction between amino acids and the corresponding alcohols using such organic acids catalysts (HX) such as sulfonic acids as methanesulfonic or p-toluenesulfonic acid. In other embodiments, other organic acid catalysts may be used.

The heating source may be employed under conventional heating (CC) between 1 hour and 3 hours at a temperature range of between 60 to 150° C. In exemplary embodiments, the temperature range is between 100 to 130° C. The product may be cooled and may be recrystallized from ethanol. The autogenous pressure depends on the employed alcohol and includes ranges from 0 to 250 psi, preferably between 0 to 180 psi.

The general synthesis scheme object of embodiments of the present invention is shown below:

Scheme 1. General scheme of synthesis of esters of ionic amino acids.

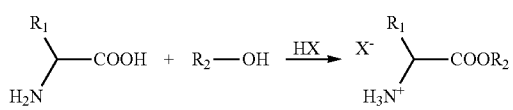

R1 and R2 represent aliphatic or branched chains of alkyl groups, functionalized alkyl or alkoxy, containing an aromatic or heterocyclic group of 1 to 10 carbon atoms for R1, preferably 1 to 6 carbon atoms to give the corresponding amino acid; R2 represents a branched chain aromatic, heterocyclic, or 6 to 20 aliphatic carbon atoms with or without unsaturation(s), preferably but not exclusively from 8 to 18 carbon atoms; and X represents an organic acid fragment like carboxylate, mesylate, or sulfonate tosylate, etc., preferably but not exclusively mesylate and tosylate.

Compounds of type 1 are preferably but not exclusively natural amino acids such as glycine, alanine and tryptophan or may be of synthetic origin.

Compounds of type 2 are preferably but not exclusively fatty alcohols with even or odd number of carbon atoms of 6 to 20 carbon atoms with or without unsaturation(s), but preferably from 8 to 18 carbon atoms, with or without unsaturation(s), branches or aryl substituents.

EXAMPLES

Some examples of the synthesis of these kind of ionic amphiphiles composed by amino acid esters are described to better illustrate the process, noting that no reagents are used in excess and which does not limit the scope of the present invention.

Example 1

Glycine (20 mmol), decyl alcohol (20 mmol) and methanesulfonic acid (24 mmol) were mixed in a Q-tube reactor equipped with a magnetic stirrer. The reactor is sealed and the reaction proceeds under vigorous stirring at 130° C. for two hours from the formation of a homogeneous mixture. After that time it was cooled and the reactor is opened, the product is diluted with hot ethanol (10 mL) and ether (25 mL) and the mixture cooled to 5° C., then filtered under vacuum. A white solid (3a) is obtained in a yield of 81% and an atom economy of 86.8% which was characterized by FTIR and $^1$H and $^{13}$C NMR.

The structure of the compound and the spectroscopic data are described below:

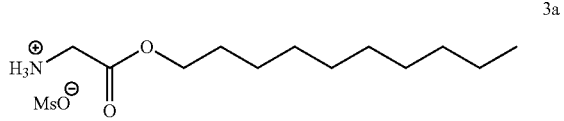

3a

Yield: 79%; mp. 67-68° C.; $^1$H NMR (CD$_3$OD): 8.34 (ws), 4.24 (t, J=6.7 Hz, 2H), 3.83 (s, 2H), 2.72 (s, 3H), 1.69 (qi, J=6.7 Hz, 2H), 1.29 (m, 14H), 0.89 (t, J=6.9 Hz, 3H); $^{13}$C-NMR: 168.3, 67.2, 40.9, 39.4, 32.8, 30.5, 30.4, 30.2, 30.1, 26.7, 23.6, 14.5; FTIR, RD-KBr (cm$^{-1}$): 3454, 3016, 2956, 2924, 1749, 1593, 1500, 1468, 1421, 1379, 1207, 1192, 1051, 904, 785.

Example 2

Glycine (20 mmol), dodecyl alcohol (20 mmol) and p-toluenesulfonic acid (24 mmol) were mixed in a Q-tube reactor equipped with a magnetic stirrer. The reactor is sealed and the reaction proceeds with vigorous stirring at 130° C. for two hours counted from a homogeneous mixture is formed. After that time, the mixture was cooled and the reactor is opened, the product is diluted with hot ethanol (10 mL) and ether (25 mL) and the mixture cooled to 5° C., then filtered under vacuum. A white solid (3b) is obtained in a yield of 74% and an atom economy of 90.6% which was characterized by FTIR and ¹H and ¹³C NMR.

The structure of the compound and the spectroscopic data are described below:

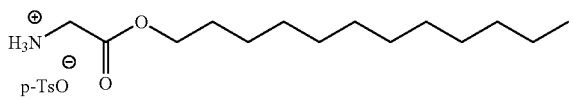

3b

Yield: 74%; mp. 129-133° C.; ¹H-NMR (CD₃OD): 8.27 (ws), 7.73 (d, J=7.7 Hz, 2H), 7.22 (d, J=7.2 Hz, 2H), 4.19 (t, J=6.8 Hz, 2H), 3.78 (s, 2H), 2.37 (s, 3H), 1.66 (qi, J=6.7 Hz, 2H), 1.28 (m, 18H), 0.89 (t, J=6.9 Hz, 3H); ¹³C-NMR: 167.6, 140.9, 139.8, 128.0, 124.9, 77.4, 76.9, 76.6, 39.0, 28.8, 28.7, 28.5, 19.9; FTIR, RD-KBr (cm⁻¹): 3467, 3223, 3059, 2954, 2920, 1751, 1595, 1506, 1443, 1242, 1161, 1124, 1038, 1012, 926, 860.

Example 3

D-alanine (20 mmol), benzyl alcohol (20 mmol) and methanesulfonic acid (24 mmol) were mixed in a Q-tube reactor equipped with a magnetic stirrer. The reactor is sealed and the reaction proceeds with vigorous stirring at 130° C. for two hours counted from a homogeneous mixture is formed. After that time, the mixture was cooled and the reactor is opened, the product is diluted with hot ethanol (10 mL) and ether (25 mL) and the mixture cooled to 5° C., the mixture is separated through decantation. A coffee oil (3c) was obtained in a yield of 76% and an atom economy of 92.1% which was characterized by FTIR and ¹H and ¹³C NMR.

The structure of the compound and the spectroscopic data are described below:

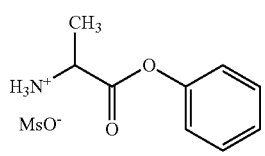

3c

Example 4

D-alanine (20 mmol), dodecyl alcohol (20 mmol) and methanesulfonic acid (24 mmol) were mixed in a Q-tube reactor equipped with a magnetic stirrer. The reactor is sealed and the reaction proceeds with vigorous stirring at 130° C. for two hours counted from a homogeneous mixture is formed. After that time, it was cooled and the reactor is opened, the product is diluted with hot ethanol (10 mL) and ether (25 mL) and the mixture cooled to 5° C., then filtered under vacuum. An oil (3d) was obtained in a yield of 85% and an atom economy of 88.8% which was characterized by FTIR and ¹H and ¹³C NMR.

The structure of the compound and the spectroscopic data are described below:

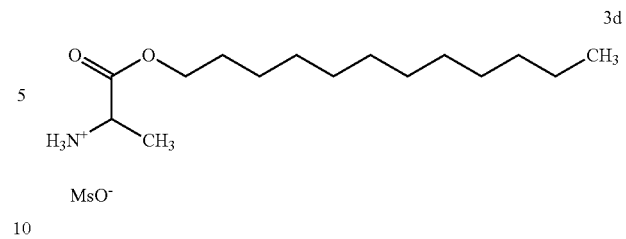

3d

Yield: 85%; mp. 73-74° C. ¹H-NMR (CD₃OD): 8.32 (ws), 7.73 (d, J=8.2 Hz, 2H), 7.22 (d, J=8.1 Hz, 2H), 3.95 (qi, J=7.3 Hz, 1 H), 3.33 (m, 2H), 2.37(s, 3H), 1.54 (d, J=7.3 Hz, 3H), 1.46 (m, 2H), 1.31 (m, 10H), 0.89 (t, J=6.7 Hz, 3H); ¹³C-NMR: 170.4, 141.0, 139.8, 130.2, 128.0, 124.9, 77.4, 76.9, 76.6, 48.1, 47.8, 47.5, 47.2, 46.9, 19.9, 19.96, 14.6; FTIR, RD-KBr (cm⁻¹): 3477, 3066, 2900, 2825, 1749, 1601, 1520, 1462, 1244, 1203, 1163, 1126, 1043, 1012, 860, 814, 688, 656.

Example 5

D-alanine (20 mmol), tetradecyl alcohol (20 mmol) and methanesulfonic acid (24 mmol) were mixed in a Q-tube reactor equipped with a magnetic stirrer. The reactor is sealed and the reaction proceeds with vigorous stirring at 130° C. for two hours counted from a homogeneous mixture is formed. After that time, it was cooled and the reactor is opened, the product is diluted with hot ethanol (10 mL) and ether (25 mL) and the mixture cooled to 5° C., then filtered under vacuum. A white solid (3e) was obtained in a yield of 86% and an atom economy of 95.4% which was characterized by FTIR and ¹H and ¹³C NMR.

The structure of the compound and the spectroscopic data are described below:

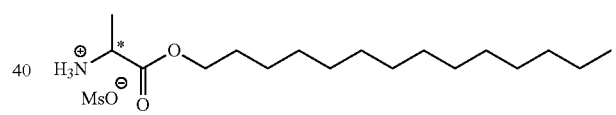

3e

Yield: 86%; mp. 86-87° C. ¹H-NMR (CD₃OD): 8.32 (ws), 7.73 (d, J=8.2 Hz, 2H), 7.22 (d, J=8.1 Hz, 2H), 3.95 (qi, J=7.3 Hz, 1 H), 3.33 (m, 2H), 2.37(s, 3H), 1.54 (d, J=7.3 Hz, 3H), 1.46 (m, 2H), 1.31 (m, 10H), 0.89 (t, J=6.7 Hz, 3H); ¹³C-NMR: 170.4, 141.0, 139.8, 130.2, 128.0, 124.9, 77.4, 76.9, 76.6, 48.1, 47.8, 47.5, 47.2, 46.9, 19.9, 19.96, 14.6; FTIR, RD-KBr (cm⁻¹): 3477, 3066, 2900, 2825, 1749, 1601, 1520, 1462, 1244, 1203, 1163, 1126, 1043, 1012, 860, 814, 688, 656.

Example 6

DL-tryptophan (20 mmol), octadecyl alcohol (20 mmol) and methanesulfonic acid (24 mmol) were mixed in a Q-tube reactor equipped with a magnetic stirrer. The reactor is sealed and the reaction proceeds with vigorous stirring at 130° C. for two hours counted from a homogeneous mixture is formed. After that time, it was cooled and the reactor is opened, the product is diluted with hot ethanol (10 mL) and ether (25 mL) and the mixture cooled to 5° C., then filtered under vacuum. A white solid (3f) was obtained in a yield of 82% and an atom economy of 93.2% which was characterized by FTIR and ¹H and ¹³C NMR.

The structure of the compound and the spectroscopic data are described below:

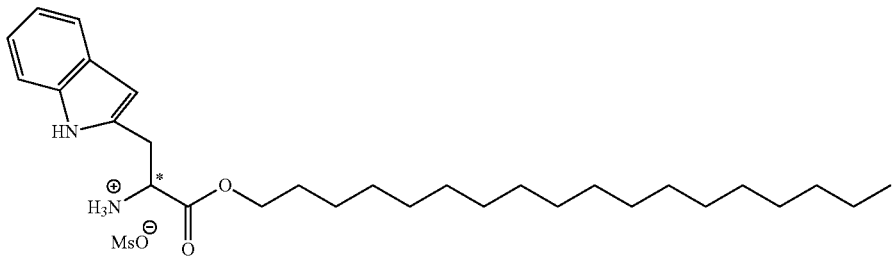

3f

Yield: 82%; decomposition p. 92° C. $^1$H-NMR (CD$_3$OD): 8.32 (ws), 7.73 (d, J=8.2 Hz, 2H), 7.22 (d, J=8.1 Hz, 2H), 3.95 (qi, J=7.3 Hz, 1 H), 3.33 (m, 2H), 2.37(s, 3H), 1.54 (d, J=7.3 Hz, 3H), 1.46 (m, 2H), 1.31 (m, 10H), 0.89 (t, J=6.7 Hz, 3H); $^{13}$C-NMR: 170.4, 141.0, 139.8, 130.2, 128.0, 124.9, 77.4, 76.9, 76.6, 48.1, 47.8, 47.5, 47.2, 46.9, 19.9, 19.96, 14.6; FTIR, RD-KBr (cm$^{-1}$): 3477, 3066, 2900, 2825, 1749, 1601, 1520, 1462, 1244, 1203, 1163, 1126, 1043, 1012, 860, 814, 688, 656.

Concluding the above, the following comparisons were made:

General Comparison between the Synthesis Reactor Pressure or Using Microwave

|  | Pressure reactor | Microwaves |
|---|---|---|
| Yield | >80% | 60-80% |
| Reaction time | 2 h | 20 min |
| Temperature | 130° C. | 70° C. |
| Amino acid/Alcohol ratio (mol/mol) | 1:1 | 1:2 |

Performance Comparison (Selected Examples)

| Amino acid, alcohol, acid | Pressure reactor | Microwaves |
|---|---|---|
| Glycine, 1-decanol, MsOH | 81% | 78% |
| Glycine, 1-dodecanol, -TsOH | 85% | 62% |
| Tryptophan, 1-octadecanol, p-TsOH | 82% | 62% |
| Alanine, bencylic alcohol | 76% | 76% |
| Alanine, 1-tetradecanol, MsOH | 86% | 75% |

In all cases, the yields in the pressure reactor are higher than those reported in microwave and no excesso of alcohol is used.

What is claimed is:

1. A process for preparing ionic amino acid esters, comprising the following synthesis route:

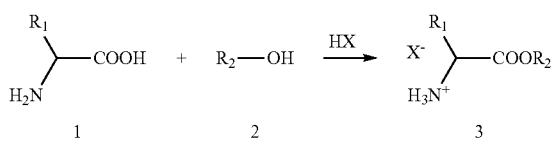

wherein R1 represents hydrogen; aromatic, aliphatic or branched alkyl; or indole-substituted alkyl;
wherein R2 represents branched alkyl; aliphatic alkyl of 6 to 20 carbon atoms with unsaturation or without unsaturation; or phenyl; and
wherein X represents a carboxylate or a sulfonate selected from a group consisting of a mesylate and a tosylate; and consisting of a single reaction step,
wherein the single reaction step consists of reacting a natural or synthetic unprotected amino acid of formula (1) with a fatty alcohol of formula (2) in stoichiometric amounts, in the presence of an organic acid (HX) selected from a group consisting of a carboxylate or a sulfonate further selected from a group consisting of a mesylate and a tosylate, employed as catalyst and under conventional heating (CC) of 1 to 3 hours at a temperature of 60 to 150° C. and pressure of 0 to 250 psi; and the ionic amino acid ester of formula (3) obtained is cooled and recrystallized from ethanol.

2. The process of claim 1, wherein the amino acid and alcohol are mixed in stoichiometric amounts with a slight excess of organic acid (HX), wherein the stoichiometric amount of the amino acid and the alcohol is less than 2 mol equivalents.

3. The process of claim 1, wherein the natural or synthetic amino acid (1) is selected from a group consisting of alanine, glycine or tryptophan.

4. The process of claim 2, wherein the natural or synthetic amino acid (1) is selected from a group consisting of alanine, glycine or tryptophan.

5. The process of claim 1, wherein the number of carbon atoms in the fatty alcohol of formula (2) used is in the range of approximately 8 to 18 carbon atoms.

6. The process of claim 2, wherein the number of carbon atoms in the fatty alcohol of formula (2) used is in the range of approximately 8 to 18 carbon atoms.

7. The process of claim 3, wherein the number of carbon atoms in the fatty alcohol of formula (2) used is in the range of approximately 8 to 18 carbon atoms.

8. The process of claim 1, wherein the organic acid catalyst (HX) is selected from the group consisting of a mesylate and a tosylate.

9. The process of claim 2, wherein the organic acid catalyst (HX) is selected from the group consisting of a mesylate and a tosylate.

10. The process of claim 3, wherein the organic acid catalyst (HX) is selected from the group consisting of a mesylate and a tosylate.

11. The process of claim 5, wherein the organic acid catalyst (HX) is selected from the group consisting of a mesylate and a tosylate.

12. The process of claim 1, wherein the reaction is carried out at a temperature in the range of approximately 100 to 130° C. and pressure in the range of approximately 0 to 180 psi.

13. The process of claim 2, wherein the reaction is carried out at a temperature in the range of approximately 100 to 130° C. and pressure in the range of approximately 0 to 180 psi.

14. The process of claim 3, wherein the reaction is carried out at a temperature in the range of approximately 100 to 130° C. and pressure in the range of approximately 0 to 180 psi.

15. The process of claim 5, wherein the reaction is carried out at a temperature in the range of approximately 100 to 130° C. and pressure in the range of approximately 0 to 180 psi.

16. The process of claim 8, wherein the reaction is carried out at a temperature in the range of approximately 100 to 130° C. and pressure in the range of approximately 0 to 180 psi.

17. The process of claim 1, wherein a yield of the obtained ionic amino acid ester of formula (3) is at least 60% and an atom economy of the obtained ionic amino acid ester of formula (3) is larger than 86.

18. The process of claim 2, wherein a yield of the obtained ionic amino acid ester of formula (3) is at least 60% and an atom economy of the obtained ionic amino acid ester of formula (3) is larger than 86.

19. The process of claim 3, wherein a yield of the obtained ionic amino acid ester of formula (3) is at least 60% and an atom economy of the obtained ionic amino acid ester of formula (3) is larger than 86.

20. The process of claim 5, wherein a yield of the obtained ionic amino acid ester of formula (3) is at least 60% and an atom economy of the obtained ionic amino acid ester of formula (3) is larger than 86.

21. The process of claim 8, wherein a yield of the obtained ionic amino acid ester of formula (3) is at least 60% and an atom economy of the obtained ionic amino acid ester of formula (3) is larger than 86.

22. The process of claim 12, wherein a yield of the obtained ionic amino acid ester of formula (3) is at least 60% and an atom economy of the obtained ionic amino acid ester of formula (3) is larger than 86.

23. The process of claim 1, where the obtained ionic amino acid esters of formula (3) are used as biosurfactants to break oil in water emulsions; to break water in oil; or to wash the crude oil contained in contaminated soils.

24. The process of claim 2, where the obtained ionic amino acid esters of formula (3) are used as biosurfactants to break oil in water emulsions; to break water in oil; or to wash the crude oil contained in contaminated soils.

25. The process of claim 3, where the obtained ionic amino acid esters of formula (3) are used as biosurfactants to break oil in water emulsions; to break water in oil; or to wash the crude oil contained in contaminated soils.

26. The process of claim 5, where the obtained ionic amino acid esters of formula (3) are used as biosurfactants to break oil in water emulsions; to break water in oil; or to wash the crude oil contained in contaminated soils.

27. The process of claim 8, where the obtained ionic amino acid esters of formula (3) are used as biosurfactants to break oil in water emulsions; to break water in oil; or to wash the crude oil contained in contaminated soils.

28. The process of claim 12, where the obtained ionic amino acid esters of formula (3) are used as biosurfactants to break oil in water emulsions; to break water in oil; or to wash the crude oil contained in contaminated soils.

29. The process of claim 17, where the obtained ionic amino acid esters of formula (3) are used as biosurfactants to break oil in water emulsions; to break water in oil; or to wash the crude oil contained in contaminated soils.

* * * * *